United States Patent [19]

Laforest nee Boutillier du Retail et al.

[11] 4,239,771
[45] Dec. 16, 1980

[54] WATER-SOLUBLE SALTS OF TIENILIC ACID

[75] Inventors: Jacqueline S. Laforest née Boutillier du Retail, Vincennes; Pierre A. R. Bessin, Chilly-Mazarin, both of France

[73] Assignee: Albert Rolland S.A., Paris, France

[21] Appl. No.: 929,114

[22] Filed: Jul. 28, 1978

[30] Foreign Application Priority Data

Aug. 4, 1977 [FR] France ............................ 77 24061

[51] Int. Cl.³ ................. A61K 31/38; C07D 333/28
[52] U.S. Cl. .................................. 424/275; 424/316; 549/70
[58] Field of Search ............ 260/329 AM, 332.3 C; 424/316, 275; 549/70

[56] References Cited

U.S. PATENT DOCUMENTS

| 2,275,809 | 3/1942 | Roberts | 424/316 |
|---|---|---|---|
| 3,758,506 | 9/1973 | Godfroid et al. | 549/70 |
| 3,958,004 | 5/1976 | Cragoe, Jr. et al. | 424/275 |
| 3,969,529 | 7/1976 | Godfried et al. | 424/275 |
| 4,001,301 | 1/1977 | Fried et al. | 260/501.14 |
| 4,017,632 | 4/1977 | Thuillier et al. | 424/275 |

FOREIGN PATENT DOCUMENTS

| 2205442 | 8/1973 | Fed. Rep. of Germany | 424/316 |
|---|---|---|---|
| 2508895 | 9/1975 | Fed. Rep. of Germany | |
| 2603890 | 8/1976 | Fed. Rep. of Germany | |
| 2196791 | 3/1974 | France | 424/316 |

OTHER PUBLICATIONS

Kirk-Othmer, "Encyclopedia of Chemical Technology", 2nd Ed., vol. 2, pp. 168-169.

Primary Examiner—Natalie Trousof
Assistant Examiner—L. Hendriksen
Attorney, Agent, or Firm—Stevens, Davis, Miller & Mosher

[57] ABSTRACT

The invention provides water-soluble salts of tienilic acid, 2,3-dichloro-4-(2-thienylcarbonyl)-phenoxyacetic acid, and amino acids of the formula

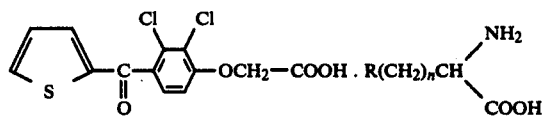

in which n is an integer of 1 to 5 and R represents a basic nitrogenous group, preferably an amino group or guanidino group. These salts, unlike the parent acid are water-soluble and are of good biodisponibility and may be used in injectable form, e.g. for emergency treatment.

7 Claims, No Drawings

WATER-SOLUBLE SALTS OF TIENILIC ACID

This invention relates to water-soluble salts of tienilic acid.

Tienilic acid, 2,3-dichloro-4-(2-thienylcarbonyl)-phenoxyacetic acid, is a diuretic and uricosuric agent used in human therapy. However, because of its water-insolubility and the insolubility of its alkali and alkaline earth metal salts, this drug can in practice only be administered to a patient orally. Consequently, the drug cannot be used in the case of an emergency when intravenous administration is essential for rapid absorption and action.

According to the present invention there are provided water-soluble salts of 2,3-dichloro-4-(2-thienylcarbonyl)-phenoxyacetic acid and an amino acid of the formula:

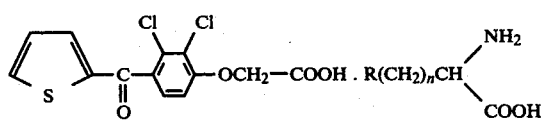

in which n is an integer of 1 to 5 and R represents a basic nitrogenous group.

R preferably represents an amino or guanidino group.

The addition salts of the invention, which have diuretic and uricosuric activity comparable with that of the parent acid compound, may be used in the preparation of aqueous injectable solutions to be administered, for example, in the treatment of pulmonary and cardiac oedemas and acute renal insufficiency. These salts, which are white crystalline powders, may also be administered, associated with known excipients, in form of pills and capsules of better biodisponibility than tienilic acid itself. The salts according to the invention are soluble in water to form stable solutions.

The amino acid portions of the salts according to the present invention contain at least one asymmetric carbon atom. Thus it will be appreciated that the salts occur in the form of optically active isomers. The present invention includes racemates and individual isomers of the salts.

The salts of the invention may be prepared by reaction, in a solvent, of tienilic acid with an amino acid of the formula

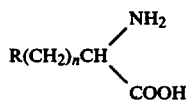

in which n and R are as defined above. The tienilic acid and amino acid are reacted in approximately equimolecular amounts. Conventional solvents such as aliphatic ketones and alcohols may be used and the reaction is generally carried out at a temperature between 5° C. and the boiling point of the solvent. The salt formed may then generally be precipitated and isolated by filtration. Optical isomers of the salts may be obtained using an optical isomer of the amino acid with the tienilic acid.

The following Examples further illustrate the present invention.

EXAMPLE 1

Lysine 2,3-dichloro-4-(2-thienylcarbonyl)-phenoxyacetate 16.55 g 2,3-Dichloro-4-(2-thienylcarbonyl)-phenoxyacetic acid and 35 ml water were added to a solution of 7.3 g 2,6-diaminohexanoic acid in 150 ml anhydrous ethanol at about 45° C. The reaction mixture was held at about 100° C. for 10 minutes and then the mixture was cooled. The cooled mixture was filtered to isolate 16 g precipitated salt. M.Pt. 225° C.

The product was shown to be an addition salt, rather than a simple mixture of tienilic acid and lysine, by infra-red spectroscopy. The product no longer showed a carboxylic band at about 1750 cm$^{-1}$.

15 g of the product salt are soluble in 100 ml of water; the pH of a solution of 5 g product salt in 100 ml of water was 6.1.

EXAMPLE 2

L (−)-Lysine 2,3-dichloro-4-(2-thienylcarbonyl)-phenoxyacetate 33.1 g 2,3-dichloro-4-(2-thienylcarbonyl)-phenoxyacetic acid and 150 ml ethanol were added at about 40° C. to a solution of 14.6 g of L (−)-lysine in 200 ml anhydrous ethanol. Using the method of Example 1, there was precipitated a salt with melting point 226° C. Again the infra-red spectrum showed than addition salt was formed. A solution of 2.5 g product salt in 100 ml water had a pH of 6.2.

EXAMPLE 3

L (+)-Arginine 2,3-dichloro-4-(2-thienylcarbonyl)-phenoxyacetate

A solution of 3.31 g 2,3-dichloro-4-(2-thienylcarbonyl)-phenoxyacetic acid and 2.1 g L (+)-1-amino-4-guanidinovaleric acid dihydrate was boiled for 15 minutes. The salt precipitated after cooling as a hemihydrate, M.Pt. 230° C.

A saturated aqueous solution (5 g in 100 ml) had a pH of 6.3.

EXAMPLE 4

Arginine 2,3-dichloro-4(2-thienylcarbonyl)-phenoxyacetate

This salt was prepared as described above.
Yield: 85%—M.Pt: 190° C.
Solubility in water: 30 g for 100 ml.
pH of concentrated aqueous solution: 6.7.

EXAMPLE 5

Ornithine 2,3-dichloro-4-(2-thienylcarbonyl)-phenoxyacetate

Using the method of Example 1, this salt was obtained at an 85% yield by reacting 13.6 g tienilic acid and 6 g 2,5-diaminopentanoic acid in ethanol. M.Pt: 230° C.

EXAMPLE 6

L (+)-Ornithine 2,3-dichloro-4-(2-thienylcarbonyl)-phenoxyacetate

Using the method of Example 5, this salt was obtained from L (+)-2,5-diaminopentanoic acid, in hemihydrate form. M.Pt: 195° C.

A saturated aqueous solution of the salt, 5 g/100 ml, had a pH of 7.4.

The salts of the present invention have toxicities comparable to that of tienilic acid itself: $LD_{50}$ for mice, per os, over 1 g/Kg. The salts according to the invention also have comparable diuretic and uricosuric activities.

The salts according to the invention may for example be administered orally or parenterally. Accordingly the invention provides pharmaceutical compositions which contain, as active ingredient, a salt according to the invention together with a pharmaceutically acceptable carrier or diluent. The daily dosage regimen, for oral administration, is from about 100 mg to about 750 mg. However as mentioned above the present salts are particularly useful in injectable form. For parenteral administration, the unit dosage is generally from about 50 to about 400 mg.

Injectable solutions may contain urea or mannitol to isotonize.

The invention also provides a method of treatment which method comprises administering to a human patient a diuretically or uricosurically effective amount of a salt according to the invention.

We claim:

1. A water-soluble salt of 2,3-dichloro-4-(2-thienylcarbonyl)-phenoxyacetic acid and an amino acid of the formula:

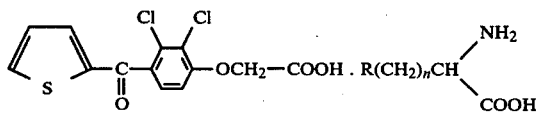

in which n is an integer of 1 to 5 and R represents an amino or guanidino group.

2. A salt according to claim 1 which is arginine 2,3-dichloro-4-(2-thienylcarbonyl)-phenoxyacetate.

3. A salt according to claim 1 which is lysine 2,3-dichloro-4-(2-thienylcarbonyl)-phenoxyacetate.

4. A salt according to claim 1 which is ornithine 2,3-dichloro-4-(2-thienylcarbonyl)-phenoxyacetate.

5. A diuretic or uricosuric composition which composition contains, as active ingredient, a diuretically or uricosurically effective amount of a water-soluble salt of 2,3-dichloro-4-(2-thienylcarbonyl)-phenoxyacetic acid and an amino acid of the formula:

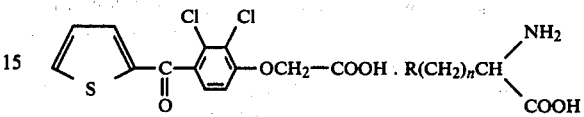

in which n is an integer of 1 to 5 and R represents an amino on guanidino group together with a pharmaceutically acceptable carrier or diluent.

6. An aqueous injectable solution according to claim 5.

7. A method of treatment which method comprises administering to a human patient in need of such treatment a diuretically or uricosurically effective amount of a water-soluble salt of 2,3-dichloro-4-(2-thienylcarbonyl)-phenoxyacetic acid and an amino acid of the formula:

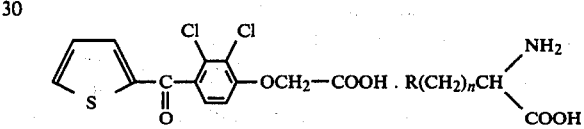

in which n is an integer of 1 to 5 and R represents an amino on guanidino group.

* * * * *